US00PP28322P3

(12) United States Plant Patent
Van Swieten

(10) Patent No.: US PP28,322 P3
(45) Date of Patent: Aug. 22, 2017

(54) ***PHALAENOPSIS* ORCHID PLANT NAMED 'PHALBUKALO'**

(50) Latin Name: ***Phalaenopsis* hybrid**
Varietal Denomination: PHALBUKALO

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 13 days.

(21) Appl. No.: 14/757,340

(22) Filed: Dec. 18, 2015

(65) Prior Publication Data

US 2017/0181350 P1 Jun. 22, 2017

(51) Int. Cl.
*A01H 5/02* (2006.01)

(52) U.S. Cl.
USPC ..... Plt./311

(58) Field of Classification Search
USPC ..... Plt./311
See application file for complete search history.

(56) References Cited

PUBLICATIONS

Enclosure for the Plant Patent application of Anthura BV, 13 pages, 2015.

*Primary Examiner* — Susan McCormick Ewoldt
(74) *Attorney, Agent, or Firm* — Jondle & Associates, P.C.

(57) ABSTRACT

A new and distinct variety of *Phalaenopsis* plant named 'PHALBUKALO', particularly characterized by having striped and netted light purple flowers, 1 to 2 peduncles, an inflorescence that is long and moderate, leaves that are oblong, and is propagated by meristem tissue culture is disclosed.

3 Drawing Sheets

Genus and species: *Phalaenopsis* hybrid.
Variety denomination: 'PHALBUKALO'.

BACKGROUND OF THE NEW PLANT

The present invention comprises a new and distinct cultivar of *Phalaenopsis* plant, botanically known as *Phalaenopsis* of the Orchidaceae family, and hereinafter referred to by the cultivar name 'PHALBUKALO'.

*Phalaenopsis* comprises a genus of about 60 species of herbaceous perennials many of which, or the hybrids thereof, are suitable for cultivar in the home or greenhouse. *Phalaenopsis* is predominantly epiphytic or rock dwelling, and is native to tropical Asia, the Malay Archipelago, and Oceania. The species typically has 2-ranked, fleshy, oblong or elliptic leaves affixed to a short central stem (monopodial growth), which vary in size from 12 to 20 cm to over 60 cm. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petals, called the labellum, are three-lobed and are often more brightly-colored than the other flower segments. Flower colors include various shades of pink, white, yellow, and red-brown.

*Phalaenopsis* orchids are typically propagated from seeds. Asexual propagation of *Phalaenopsis* is often done from off-shoots which arise from the lower bracts of the inflorescence. The resulting plants are detached from the mother plants and may be planted in a suitable substrate.

The new *Phalaenopsis* 'PHALBUKALO' is particularly characterized by its attractive and unique striped and netted light purple flowers, economical propagation by tissue culture, rapid growth, and a plant dimension suitable for packaging and shipping to the market.

'PHALBUKALO' is a product of a planned breeding program conducted by the inventor in Bleiswijk, The Netherlands.

The new *Phalaenopsis* 'PHALBUKALO' originated from a cross made in April 2001 in Bleiswijk, The Netherlands. The female parent is an unknown *Phalaenopsis* pot plant named 'unknown' (unpatented), while the male parent is an unknown *Phalaenopsis* pot plant named 'unknown' (unpatented). A single plant was selected in May 2004 and has been asexually reproduced repeatedly by meristem tissue culture in Bleiswijk, The Netherlands over a 7.5-year period. The new variety has been found to retain its distinctive characteristics through successive asexual propagations.

Asexual reproduction of 'PHALBUKALO' by tissue culture was first performed in April 2008 in Bleiswijk, The Netherlands and has demonstrated that the new cultivar is firmly fixed and retained through successive generations of asexual reproduction.

Plant Breeder's Rights for this variety have been applied for in Europe on Dec. 11, 2014. 'PHALBUKALO' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands.

1) Striped and netted light purple flowers;
2) 1 to 2 peduncles;
3) Inflorescence is long and moderate;
4) Shape of the leaf is oblong; and
5) Plants are propagated by meristem tissue culture.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs are of a 50-week old plant grown in a greenhouse in Bleiswijk, The Netherlands in July 2015.

DESCRIPTION OF THE NEW VARIETY

Figure 1:
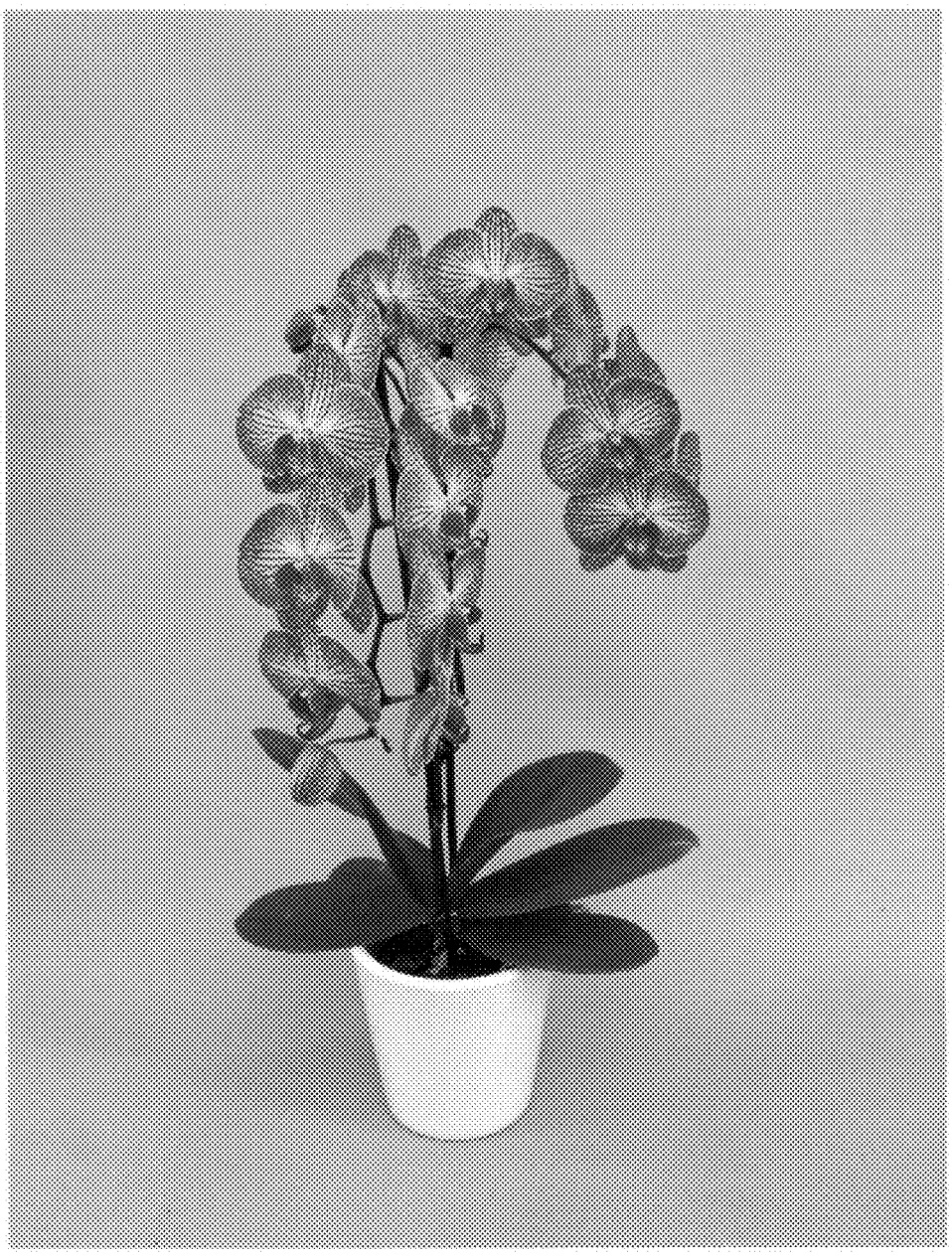
FIG. 1 shows the overall plant habit, including blooms, buds and foliage of 'PHALBUKALO'.
Figure 2:
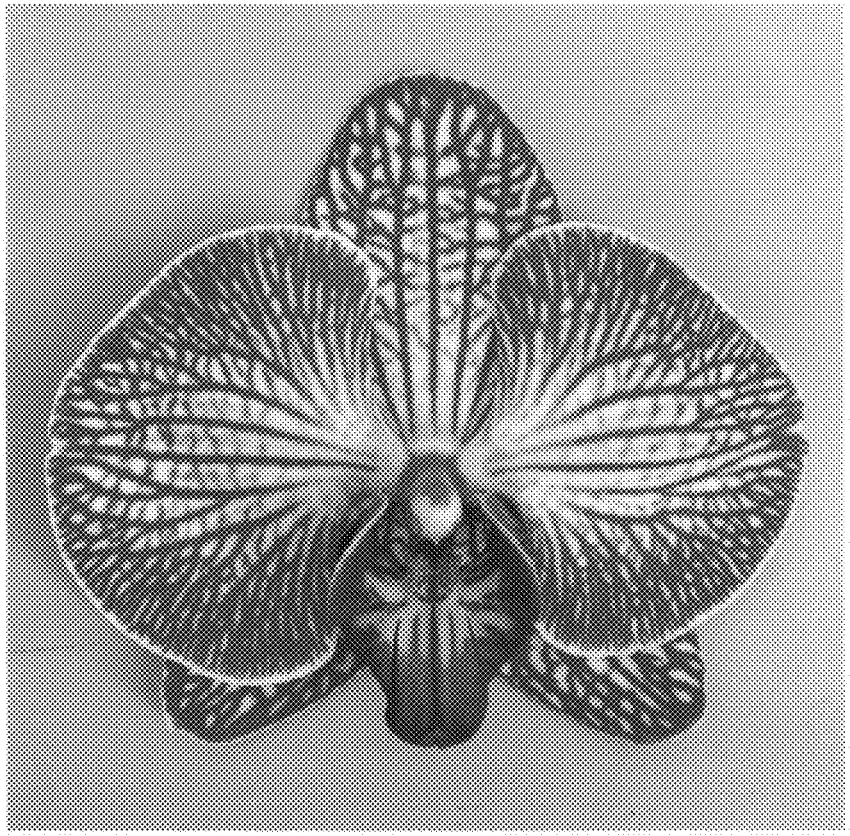
FIG. 2 shows a close-up of a flower of 'PHALBUKALO'.
Figure 3:
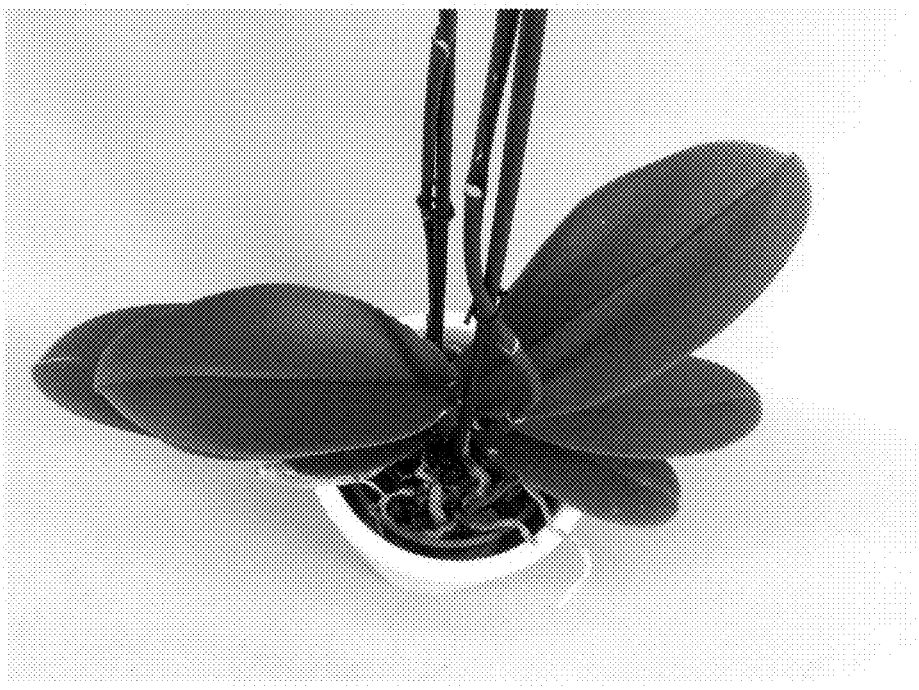
FIG. 3 shows a close-up of the leaves of 'PHALBUKALO'.

The following detailed description sets forth the distinctive characteristics of 'PHALBUKALO'. The data which define these characteristics were collected from asexual reproductions carried out in Bleiswijk, The Netherlands. The plant history was taken on 50-week old plants which were planted from a nursery tray in 12 centimeter pots and grown in a greenhouse between 27° C. to 29° C. for 30 weeks, continued by a cooling period of 8 weeks between 18° C. to 20° C. and 12 weeks in a greenhouse of 21° C. Observations were made in August 2015. Color readings were taken under 4-6000 lux natural light in the greenhouse. Color references are primarily to The R.H.S. Colour Chart of The Royal Horticultural Society of London (R.H.S.) (1995).

DETAILED BOTANICAL DESCRIPTION

Classification:
- *Family*.—Orchidaceae.
- *Botanical*.—*Phalaenopsis* hybrid.
- *Common name*.—*Phalaenopsis*.
- *Variety name*.—'PHALBUKALO'.

Parentage:
- *Female parent*.—*Phalaenopsis* cultivar 'unknown' (unpatented).
- *Male parent*.—*Phalaenopsis* cultivar 'unknown' (unpatented).

Propagation:
- *Type*.—Meristem tissue culture.

Plant:
- *Crop time* (*time to produce a finished flowering plant*).—48 to 50 weeks for a 12 cm pot.
- *Growth habit of peduncle*.—Standard, green leaves, raceme to panicle.
- *Height* (*including pot, including inflorescence*).—58.0 cm to 68.0 cm.
- *Width* (*measured from leaf tips*).—32.0 cm to 34.0 cm.
- *Vigor*.—Moderate.

Roots:
- *Root description*.—Grey-green colored roots with branching lateral roots having light green-purple colored root tips.

Leaves:
- *Mature leaves*.—Quantity per plant: 8 to 10 leaves are produced before flowering. Length (fully expanded): 15.0 cm to 18.0 cm. Width: 7.5 cm to 8.5 cm. Shape: Oblong. Base shape: Moderately elongated. Apex: Obtuse to rounded unequal. Leaf blade angle with the petiole (measured from the horizontal position): Between 20 degrees and 60 degrees. Leaf margin: Entire. Color: Upper surface: RHS 147A with a small lighter edge RHS 146A. Lower surface: RHS 146B and RHS 147B. Texture: Rough. Thickness: 2.5 mm to 3.0 mm. Venation: Pattern: Parallel. Color of the midvein: Upper surface: mix of RHS 146A and 147B. Lower surface: RHS 146B.

Peduncle:
- *Quantity per plant*.—1 to 2.
- *Number of flowers per peduncle*.—10 to 15.
- *Length*.—50.0 cm to 55.0 cm.
- *Diameter*.—5.4 mm to 5.7 mm.
- *Strength*.—Strong.
- *Aspect*.—Upright to pendant.
- *Texture*.—Slightly rough.
- *Color*.—Mix of brown (RHS 200A) and green (RHS 146B).
- *Internode length*.—35.0 mm to 45.0 mm.
- *Callosities*.—None.

Inflorescence description:
- *Appearance*.—Upright to slightly pendant, raceme to panicle inflorescence with bilaterally symmetrical flowers that open in succession beginning with the lowermost flower.
- *Inflorescence size*.—Height (from base to tip): 250.0 mm to 300.0 mm.
- *Flowering time*.—First flowers can be expected 10 to 11 months after planting in a 12 cm pot.
- *Flower*.—Height: 80.0 mm to 85.0 mm. Diameter: 85.0 mm to 90.0 mm. Depth of lip: 22.0 mm to 25.0 mm.
- *Flower longevity*.—On the plant: 7 to 9 weeks.
- *Fragrance*.—Absent.
- *Flower bud*.—Average size: Medium to large. Length: 20.0 mm to 22.0 mm. Width: 17.0 mm to 19.0 mm. Shape: Egg shaped. Color: Mix of green (RHS 146D) and greyed-purple (RHS 186A) striped (RHS 79A and 80A).
- *Petals*.—Arrangement: Open/free. Shape: Semi-circular. Apex: Slightly emarginated asymmetric. Margin: Entire to slightly undulate. Length (from base to tip): 39.0 mm to 41.0 mm. Width: 52.0 mm to 54.0 mm. Color (when fully opened): Upper surface: Basic color: Light purple (RHS 78C) striped and netted (RHS 78A) with a small white edge (RHS 155C). Over color: Absent. Lower surface: Basic color: White (RHS 155C) striped (RHS 80A). Over color: Light purple (RHS 78D).
- *Dorsal sepal*.—Shape: Elliptic. Apex: Rounded symmetric. Margin: Entire. Length (from base to tip): 44.0 mm to 46.0 mm. Width: 30.0 mm to 32.0 mm. Color (when fully opened): Upper surface: Basic color: White (RHS 155C) netted (RHS 78A). Over color: Light purple (RHS 78B). Lower surface: Basic color: Light purple (RHS 78D) striped and netted on the edge (RHS 80D). Over color: absent.
- *Lateral sepals*.—Shape: Ovate. Apex: Obtuse asymmetric. Margin: Entire. Length (from base to tip): 42.0 mm to 44.0 mm. Width: 26.0 mm to 28.0 mm.

Color (when fully opened): Upper surface: Basic color: White (RHS 155C) netted and dotted at the base (RHS 78A). Over color: Light green at the base (RHS 145C to 145D). Lower surface: Basic color: Light purple (RHS 78D and 76C) striped and slightly netted on the edge (RHS 80A). Over color: Touch of green at the base (RHS 145B and 145C).

*Labellum* (*lip*).—Margin: Entire. Whiskers: Present. Length of whiskers: 15.0 mm to 17.0 mm. Color of whiskers: Dark purple (RHS 79A and 80A) with small white tips (RHS 155C). Pubescence on the lip: Absent.

*Lateral lobe*.—Shape: Type V (as described in the International Union for the Protection of New Varieties of Plants (UPOV) Test Guidelines for Phalaenopsis); spatulate. Length (from base to tip): 20.0 mm to 22.0 mm. Width: 14.0 mm to 16.0 mm. Color: Purple (RHS 78A) and red-purple (RHS 59A) with a touch of white (RHS 155C) and yellow at the base (RHS 12A).

*Apical lobe*.—Shape: Triangular. Length (from base to tip): 19.0 mm to 21.0 mm. Width: 23.0 mm to 25.0 mm. Color: Purple (RHS 78A) with yellow (RHS 4C) and white (RHS 155C) at the base.

*Callus*.—Height: 0.5 cm to 0.7 cm. Length: 0.6 cm to 0.8 cm. Width: 0.3 cm to 0.5 cm. Color: Yellow (RHS 13A) dotted (RHS 175B).

Reproductive organs:

*Arrangement*.—The stamens, style and stigmas are fused into a single, short structure called the column, possessing one terminal anther with pollen grains united into pollinia, which are covered by an anther cap. The stigma is located under the column behind the pollinia. The ovary is inferior with three carpels present.

*Column*.—Length: 10.0 mm to 12.0 mm. Diameter: 4.6 mm to 5.1 mm. Color: Purple (RHS 78B) with white top (RHS 155C).

*Pollinia*.—Quantity: 2. Size: 1.0 mm to 1.2 mm. Color: Orange (RHS 26A).

*Ovary*.—Part of the pedicel with small ribs towards the column. Length: 7.0 mm to 9.0 mm. Diameter: 2.2 mm to 2.4 mm.

*Pedicel*.—Length: 33.0 mm to 35.0 mm. Diameter: 2.6 mm to 2.9 mm. Color: Greyed-purple (RHS 183D) from the inflorescence; green (RHS 146D and 145B to 145C) and light purple (RHS 75A to 75C) towards the flower.

Disease, pest, and stress resistance: No specific resistance or susceptibility observed.

Temperature tolerance: Tolerant to a low temperature of 15° C. and a high temperature of about 30° C.

COMPARISON WITH PARENTAL AND COMMERCIAL VARIETIES

The female parent of 'PHALBUKALO' is unknown, therefore a comparison can not be made.

The male parent of 'PHALBUKALO' is unknown, therefore a comparison can not be made.

'PHALBUKALO' differs from commercial variety 'PHALPNIZOK' (unpatented) in that the lower surface of the lateral lobe lip of 'PHALBUKALO' is a mix of purple and greyed-purple with a touch of yellow on one side and slightly white at the base, whereas the lower surface of the lateral lobe lip of 'PHALPNIZOK' is a mix of white and diluted purple with yellow and greyed-purple edge on one side. Additionally, 'PHALBUKALO' has petals with emarginated apex and flowers that are darker colored than 'PHALPNIZOK', whereas 'PHALPNIZOK' has petals with obtuse apex and flowers that are lighter colored than 'PHALBUKALO'.

I claim:

1. A new and distinct variety of *Phalaenopsis* plant named 'PHALBUKALO', substantially as described and illustrated herein.

* * * * *